United States Patent [19]
Hildebrand et al.

[11] Patent Number: 5,486,176
[45] Date of Patent: Jan. 23, 1996

[54] ANGLED BONE FIXATION APPARATUS

[75] Inventors: Bryan D. Hildebrand, Cleveland Heights, Ohio; Laura C. Small, Memphis, Tenn.; Hansen A. Yuan, Fayetteville, N.Y.; B. Thomas Barker; Matthew M. Morrison, both of Memphis, Tenn.; Abraham Salehi, Bartlett, Tenn.; Forrest C. Smith, Collierville, Tenn.

[73] Assignee: Smith & Nephew Richards, Inc., Memphis, Tenn.

[21] Appl. No.: 200,700

[22] Filed: Feb. 23, 1994

Related U.S. Application Data

[63] Continuation-in-part of Ser. No. 856,707, Mar. 24, 1992, abandoned, and Ser. No. 62,825, May 14, 1993, abandoned, each is a continuation-in-part of Ser. No. 675,740, Mar. 27, 1991, Pat. No. 5,129,899.

[51] Int. Cl.$^6$ .......................... A61B 17/80; A61B 17/70
[52] U.S. Cl. .................................. 606/71; 606/61
[58] Field of Search ................. 606/61, 60, 69, 606/70, 71; 403/3, 4, 13, 14

[56] References Cited

U.S. PATENT DOCUMENTS

| | | |
|---|---|---|
| 2,406,832 | 9/1946 | Hardinge . |
| 3,244,170 | 4/1966 | McElvenny . |
| 3,596,656 | 8/1971 | Kaute . |
| 3,648,691 | 3/1972 | Lumb et al. . |
| 3,741,205 | 6/1973 | Markolf et al. . |
| 4,135,506 | 1/1979 | Ulrich . |
| 4,246,660 | 1/1981 | Wevers . |
| 4,289,123 | 9/1981 | Dunn . |
| 4,369,769 | 1/1983 | Edwards . |
| 4,433,677 | 2/1984 | Ulrich et al. . |
| 4,524,765 | 6/1985 | de Zbikowski . |
| 4,604,995 | 8/1986 | Stephens et al. . |
| 4,611,581 | 9/1986 | Steffee . |

(List continued on next page.)

FOREIGN PATENT DOCUMENTS

| | | | |
|---|---|---|---|
| 0506420 | 9/1992 | European Pat. Off. . | |
| 829103 | 5/1981 | U.S.S.R. | ................................ 606/71 |
| 860756 | 9/1981 | U.S.S.R. | ................................ 606/71 |
| 923532 | 4/1982 | U.S.S.R. | ................................ 606/71 |
| 959771 | 9/1982 | U.S.S.R. | ................................ 606/71 |
| 984468 | 1/1983 | U.S.S.R. | ................................ 606/59 |
| 1616643 | 12/1990 | U.S.S.R. . | |

OTHER PUBLICATIONS

Gray, Henry, 1901 Ed. *Anatomy, Descriptive and Surgical*, pp. 34–54, Running Press, Philadelphia, Pennsylvania.

Wenz, L. M. et al., "Accelerated Testing of a Composite Spine Plate," in *Composites*, vol. 20, No. 6, Nov. 1989, pp. 569–574.

*Primary Examiner*—Tamara L. Graysay
*Attorney, Agent, or Firm*—Pravel, Hewitt, Kimball & Krieger

[57] ABSTRACT

An angled bone fixation apparatus including a bone screw having a first end portion adapted to be surgically implantable into a patient's vertebral bone mass and at first and second spaced apart positions on the bone mass and a second end portion having a head portion with a load transfer surface thereon and a top surface. An elongated plate member having upper and lower surfaces angled with respect to each other and an elongated plate slot having a longitudinally extending axis with the slot being surrounded by a peripheral portion having outer opposed edges. The plate member has a first and second angled sidewall at the slot with the sidewalls each forming an acute angle with the upper and lower plate surfaces. A washer interfaces with the plate member and the bone screw, for distributing load from the bone screw to the plate member with the washer including an opening and upper and lower surfaces with the lower surface having a pair of spaced apart projections extending therefrom. The plate member having a plurality of adjustment openings with each of the washer projections sized and shaped to fit in selected pairs of the adjustment openings.

21 Claims, 3 Drawing Sheets

U.S. PATENT DOCUMENTS

| | | | |
|---|---|---|---|
| 4,641,636 | 2/1987 | Cotrel . | |
| 4,653,481 | 3/1987 | Howland et al. . | |
| 4,696,290 | 9/1987 | Steffee . | |
| 4,773,402 | 9/1988 | Asher et al. . | |
| 4,887,595 | 12/1989 | Heinig et al. | 606/61 |
| 4,887,596 | 12/1989 | Sherman | 606/61 |
| 4,913,134 | 4/1990 | Luque | 606/61 X |
| 4,987,892 | 1/1991 | Krag et al. | 606/61 |
| 5,041,113 | 8/1991 | Biedermann et al. | 606/61 |
| 5,053,036 | 10/1991 | Perren et al. | 606/69 |
| 5,092,893 | 3/1992 | Smith | 623/17 |
| 5,108,395 | 4/1992 | Laurain | 606/61 |
| 5,127,912 | 7/1992 | Ray et al. | 606/61 |
| 5,129,899 | 7/1992 | Small et al. | 606/61 |
| 5,147,360 | 9/1992 | Dubousset | 606/61 |
| 5,152,303 | 10/1992 | Allen | 128/898 |

ANGLED BONE FIXATION APPARATUS

This is a continuation-in-part application of prior, U.S. patent application Ser. No. 07/856,707 filed Mar. 24, 1992 now abandoned and U.S. patent application Ser. No. 08/062,825 filed May 14, 1993 now abandoned, which are continuation-in-part applications of Ser. No. 675,740, filed may 27, 1991, now U.S. Pat. No. 5,129,899 issued Jul. 14, 1992, all incorporated herein by reference.

FIELD OF THE INVENTION

The present invention relates to posterior cervical surgery and more particularly to an improved fixation apparatus for placing bone screws so that a more effective transmission of force from a vertebrae, through a screw/plate construct and back into a vertebrae may exist.

BACKGROUND OF THE INVENTION

There are a number of surgical procedures which require a fixation of portions of the spine with respect to one another. Typically, bone screws are employed in the fixation of the spine. The implantation of bone screws is a surgical procedure which involves the formation of one or more surgical openings in adjacent portions of the spine, with threaded bone screws being implanted into the surgical openings. Connective structures such as rods or plates extend between the various spine members by connecting the adjacent bone screws.

An early spinal fixation system can be seen in the Lumb et al. U.S. Pat. No. 3,648,691 entitled "Method of Applying Vertebral Appliance". In the Lumb patent, a method of applying a vertebral appliance for use in bridging one or more diseased or damaged vertebra uses a pair of elongated flexible multiple aperatured plates having fasteners which are used to clamp the plate to opposite sides of the spinous processes being spanned. Each strap or plate is of a length adapted to span at least two spinous processes and project there beyond each end so that the fasteners can be passed both behind and in front thereof as well as through the interspinous gap there between. The apertures are located considerably closer together than adjacent processes and they are fastened to the latter in position such that at least one opening registers with each one to receive a growth or soft bony tissue that eventually extrudes therein.

A U.S. Pat. No. 4,369,769 to Edwards shows a spinal fixation system using elongated rods used to bridge across various portions of the spine. In the Edwards '769 patent a spinal fixation device is provided in which sleeves or spacers are placed over and around spinal rods in order to obtain a better reduction of spinal fractures or spinal deformities. These sleeves can be made in various thicknesses so that the surgeon can obtain optimum fixation in each case. The sleeves are made of any biologically compatible material.

Use of bone screws and connecting rods is also seen in the Ulrich et al. U.S. Pat. No. 4,433,677 entitled "Implantable Splint for Correction Lumbosacral Spondylodesis". In the Ulrich patent a spinal distraction splint has two like anchor screws extending along respective longitudinal screw axes and adapted to be anchored in the pelvis with the axes crossing. Each of the screws has a head formed with a transverse open recess centered on respective transverse axis and with an angular array of teeth centered on and angularly spaced about the respective transverse axis.

Another patent that shows screws as part of a spinal stabilizer is the Stephens et al. U.S. Pat. No. 4,604,995. In the Stephens patent a surgical implant is used for imparting stability to the thoraco-lumbar spine by fixation of the implant to the spine with segmental spinal instrumentation. The implant comprises a unitary rod having a generally rectangular configuration formed by a pair of spaced apart branches, mirror image duplicated of one another and equally spaced apart along their length.

A U.S. Pat. No. 4,611,581 to Steffee entitled "Apparatus for Straightening Spinal Columns" provides an apparatus to reduce the extent of displacement between adjacent vertebra in a person's spinal column and to subsequently maintain the vertebra in a reduced displacement relationship. When the apparatus is to be installed, holes are formed in the displaced vertebra and in vertebra on opposite sides of the displaced vertebra. Force transmitting members are mounted in the holes in the vertebra. A spinal plate is then positioned on the spinal column with the force transmitting members extending outwardly through the slots in the spinal plate. Nuts are tightened on the force transmitting members connected with vertebra on opposite sides of the displaced vertebra to anchor the spinal plate in place. A nut on the force transmitting member connected with the displaced vertebra is then tightened to pull the displaced vertebra to a desired position. In one embodiment, the force transmitting member has a relatively large diameter helix which engages a side wall of the hole in the displaced vertebra. In another embodiment, an insert is positioned in a hole in the displaced vertebra and expanded by the force transmitting member to securely grip the vertebra.

A device which uses clamps as opposed to bone screws is the Asher U.S. Pat. No. 4,773,402 entitled "Dorsal Transacral Surgical Implant" wherein a pair of spine engageable rods, contoured to the desired spinal column configuration are provided with a yoke and foot element being attached to the pair of rods during use.

The Sherman U.S. Pat. No. 4,887,596 shows a pedicle screw for use in internal fixation of the spine comprising a shaft threaded at one end for insertion into a bone and at the other end having a yoke for receiving a rod, the yoke having a cusp adapted to bear against the rod and clamps for holding the rod against the cusp while permitting adjustment of the angle between the rod and the yoke.

One of the problems with the application of a spinal fixation system is the adjustability of the connective structures such as the plate with respect to a plurality of spaced-apart bone screws. Another problem with the application of a spinal fixation system is the placement of such a system in the cervical region. In the cervical region such as a posterior cervical spine application, anatomical fit and the lack of massive bone present an even greater problem of adjustability and adequate fixation.

The surgical techniques for treating cervical instability are similar to treating other problems of spinal instability. However, specific treatments vary widely with both the anterior and posterior approach. The options available to the surgeon when treating spinal instability include but are not limited to wiring, bone screws, and plate/screw constructs. For instability that spans several vertebrae, plates/screw constructs are the most used.

In order to fulfill the requirements of cervical anatomy as well as the differing lumbar and cervical anatomy on many patients, a medical device such as a plate/screw mechanism, is needed that provides variability in screw placement and angulation of the screw in order to provide effective treatment of the spine.

SUMMARY OF THE INVENTION

The object of the present invention is to provide an angled bone plate and washer mechanism that maximizes medial/lateral angulation, longitudinal angulation and variability in the placement of the screw. With the apparatus of the invention, the screw position is varied by manipulating a pegged washer on a plate having mating peg holes. The peg holes are located on the plate a consistent distance apart and a washer is fitted in the pegged plate holes to accommodate the vertebral anatomy for optimal screw placement. Additionally, the washer's pegged centerlines are offset from the spherical countersunk centerline on the washer that cradles the screw head. This offset allows for fine adjustment between the screw location on the plate and washer to screw location in the vertebrae by rotating the washer 180° about the screw head. The plate is provided with an asymmetrical cross-section which provides a better anatomical fit.

BRIEF DESCRIPTION OF THE DRAWINGS

For a further understanding of the nature and objects of the present invention, reference should be made to the following detailed description taken in conjunction with the accompanying drawings, in which like parts are given reference numerals, and wherein.

DETAILED DESCRIPTION OF A PREFERRED EMBODIMENT

Figure 3:
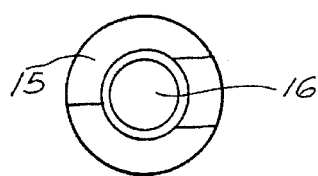
FIG. 3 is a top plan view of the screw of FIG.
Figure 2:
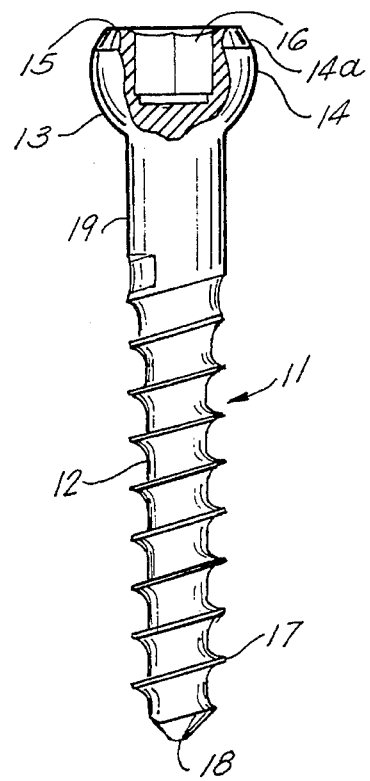
FIG. 2 is side plan view of a screw of the apparatus of the present invention.
Figure 1:
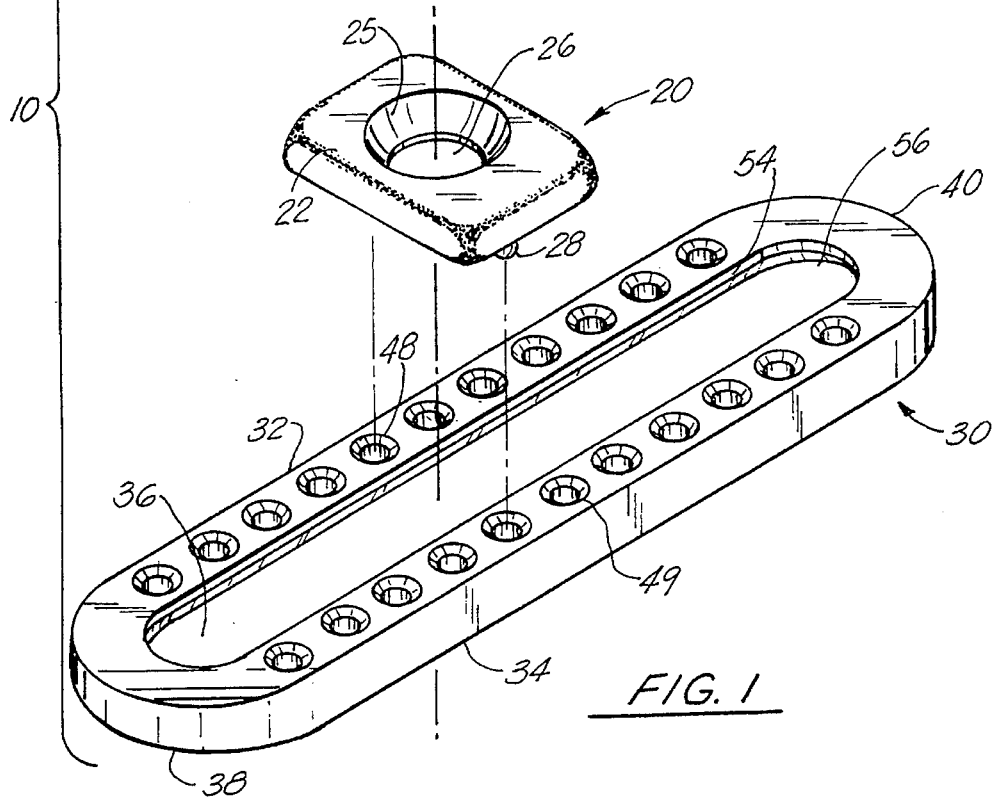
FIG. 1 is a perspective exploded view of the preferred embodiment of the apparatus of the present invention.
Figure 11:
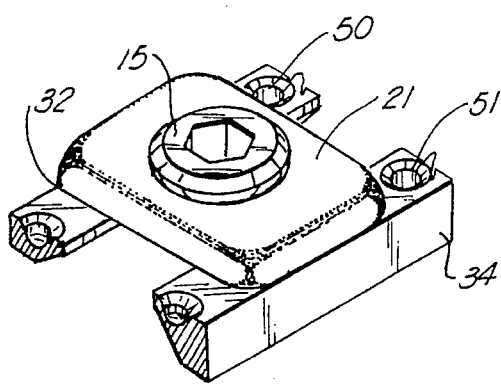
FIG. 11 is a fragmentary perspective view of the apparatus of the present invention.

FIG. 1 shows the preferred embodiment of the present invention designated generally by the numeral 10. Bone fixation apparatus 10 includes a bone screw 11, a washer 20 and a plate 30. Bone screw 11 (FIG. 2) has an elongated shank 12 with an enlarged head portion 13 affixed to one end of the shank 12. The enlarged head 13 has a generally hemispherically shaped surface 14 on the underside of the head 13 and a top surface 15. The hemispherically shaped surface 14 begins at cylindrical surface 19 and ends at top surface 15. An annular beveled surface 14a forms an interface between the surface 14 and the surface 15. A tool receptive socket such as hexagonal socket 16 is provided on the flat top surface 15, so that the bone screw 11 can be rotated using a hexagonal wrench or other such tool or instrument (FIG. 11).

The lower tip 18 of the bone screw 11 communicates with a helical thread 17 that begins at the lower tip 18 and terminates at a cylindrical surface 19. The cylindrical surface 19 and hemispherical surface 14 interface with washer 20 at opening 26 (see FIGS. 7 and 13) as will be described more fully hereinafter.

Figure 5:
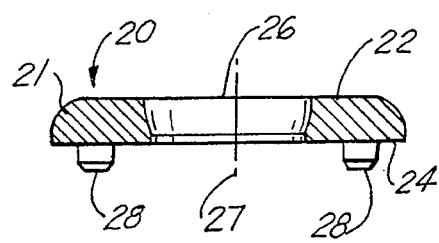
FIG. 5 is side cross-sectional view of the washer of FIG. 4.
Figure 6:
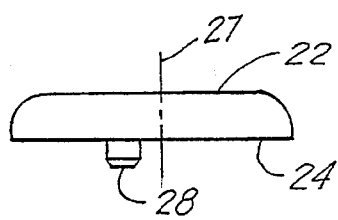
FIG. 6 is a side plan view of the washer along site lines 6—6 of FIG. 4.
Figure 12:
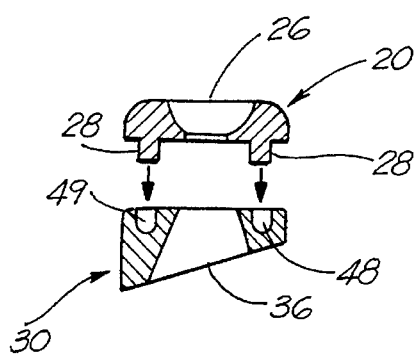
FIG. 12 is a cross-sectional view of a portion of the apparatus of the present invention.

Washer 20 provides a transverse plate member 21 having an upper surface 22 and a lower surface 24. A central opening 26 with a countersunk annular wall 25 and a centerline 27 extends between the upper surface 22 and lower surface 24 of the plate member 21 FIGS. 1, 5 and 6). Spaced apart projections 28 extend below the bottom surface 24 of the plate member 21. The projections 28 could be teeth or pegs, however, in a preferred embodiment the projections 28 are a pair of generally cylindrically-shaped pegs (FIGS. 5 and 6). Pegs 28 are sized, shaped and spaced apart such that when washer 20 engages plate 30, the pegs 28 register in selected openings on the plate 30 (FIG. 12).

Figure 4:
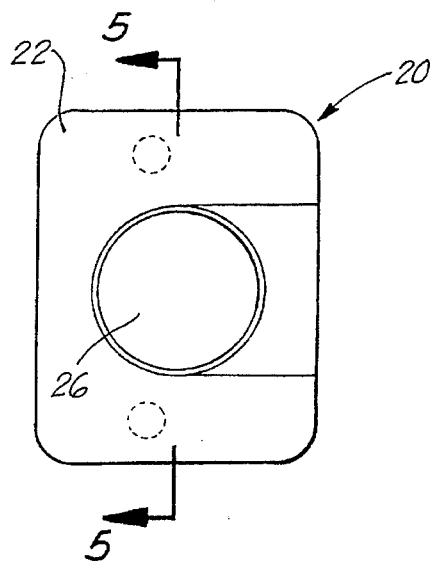
FIG. 4 is a top plan view of a washer of the apparatus of the present invention.

As shown in FIGS. 4 and 6, pegs 28 are offset from the centerline 27 of washer opening 26 which allows the washer 20 to be placed on the plate 30 in an offset position. The pegs 28 could also be offset from each other as well as offset from the centerline 27 of the washer opening 26. Displacement of the opening centerline 27 and thus the screw 11 centerline, is possible by simply rotating the washer 180° while keeping the washer pegs 28 in the same location on the plate 30. The orientation of the pegs 28 in relation to the washer opening 26 allows for fine adjustment between the screw location on the plate and washer to screw location in the vertebrae by rotating the washer 20 180° about the screw head 13.

Figure 7:
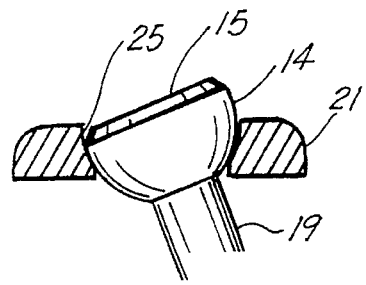
FIG. 7 is fragmentary partial cross-sectional view of a portion of the apparatus of the present invention.

The countersunk wall 25 of the washer opening 26 and the size of the hemispherical surface 14 of the screw head 13 allow the screw 11 to rotate in the washer opening 26 such that part of the top surface 15 of the screw head 13 can angulate below the upper surface 22 of the washer 20 (FIG. 7).

Figure 8:
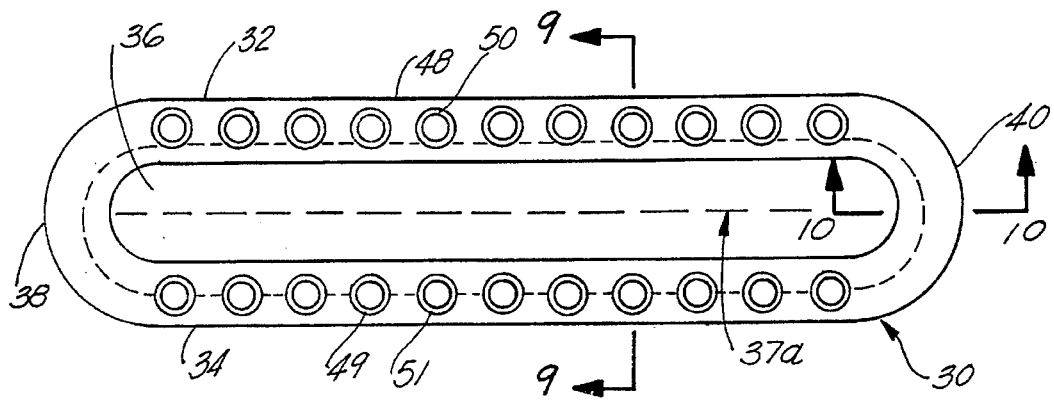
FIG. 8 is a top plan view of a plate of the apparatus of the present invention.
Figure 9:
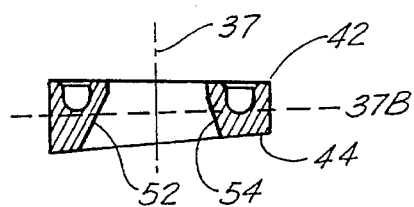
FIG. 9 is a cross-sectional view of the plate of the apparatus along site lines 9—9 of FIG. 8.
Figure 10:
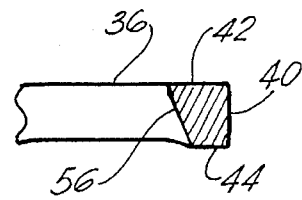
FIG. 10 is a cross-sectional view of the plate of the apparatus along site lines 10—10 of FIG. 8.

Plate 30 has generally flat, parallel opposed outer walls 32, 34 with a central longitudinally extending slot 36 and generally semi-circular end portions 38, 40 (FIGS. 1 and 8). Plate 30 has a centerline 37, a longitudinal axis 37a and a transverse cross section 37b (FIGS. 8 and 9). Plate 30 provides an upper surface 42 and a lower surface 44, each communicating with slot 36. The upper surface 42 of the plate 30 includes a plurality of spaced-apart blind openings 48, 49, 50, 51 respectively. Each of the openings 48–51 are sized and shaped to register with the pairs of pegs 28 on the washer 20 when the washer 20 engages plate 30. Because pegs 28 are offset with the centerline 27 of the washer 20, allowing washer 20 to be rotated 180°, only half the number of openings 48–51 are required in order to provide a greater amount of resolution for screw 11 placement in relation to the washer 20 and the plate 30 and the bone mass.

In a preferred embodiment, as shown in FIG. 9, plate 30 is also provided with an asymmetrical cross-section (such as trapezoidal, for example) which provides a more anatomically correct placement of the plate 30 on the lateral masses of the vertebral bone.

The plate 30 includes slot sidewalls 52, 54 which form an acute angle between the upper and lower surfaces 42, 22.

The sidewalls 52, 54 angle out toward the outer walls 32, 34, causing slot 36 to be wider at the lower surface 44 as shown in FIG. 9. Sidewall 52 is angled between about 15° to 45° and in a preferred embodiment 25° relative to the centerline 37 of plate 30. Sidewall 54 is angled between about 15° to 45° and in a preferred embodiment 20° relative to the centerline 37 of plate 30. The slot sidewall 56, at the semi-circular end portions 38, 40 is angled between about 15° to 30° relative to the transverse cross section 37b of the plate 30.

Figure 13:
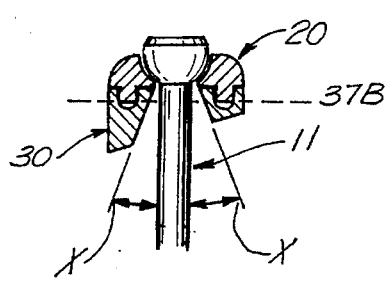
FIG. 13 is a fragmentary partial cross-sectional view of the apparatus of the present invention.
Figure 14:
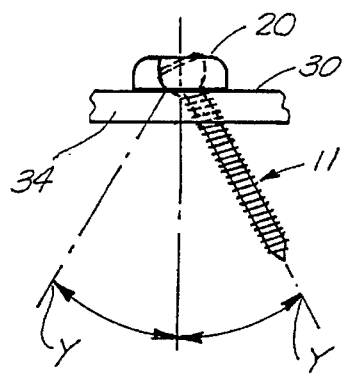
FIG. 14 is a schematic cross-sectional view of the apparatus of the present invention.

The angulation of the sidewalls 52, 54 provides for a certain amount of constriction in the range of angulation of the screw 11 in the medial/lateral plane as illustrated in FIG. 13. The washer 20 in combination with the transverse cross section 37b and longitudinal axis 37a of the plate 30 allows the screw 11 to have an elliptical rotational range of between about 20° to 80°, defined by X—X, in the medial/lateral plane as illustrated in FIG. 13 and between about 20° to 80°, defined by Y—Y, in the cephalad/caudal plane as illustrated in FIG. 14.

The bone fixation apparatus 10 is assembled by placing washer 20 upon plate 30 such that pegs 28 register in a selected opening 48 and 49 respectively. The lower surface 24 of washer 20 aligns with the upper surface 42 of the opposed outer walls 32, 34 of the plate 30. When the washer 20 is placed over the plate 30, the center of the washer opening 26 registers with the centerline 37 of the plate slot 36. The bone screw 11 is inserted through the washer opening 26 and implanted into the spine allowing for the proper placement, alignment and angulation necessary for effective treatment of the spine.

It should be understood that there can be improvements and modifications made to the embodiments of the invention described in detail above without departing from the spirit or scope of the invention, as set forth in the accompanying claims.

What is claimed is:

1. An angled bone fixation apparatus, comprising:
   a) a plurality of bone screws having a first end portion and a second end portion, said first end portion configured to be surgically implantable into a patient's vertebral bone mass and at first and second spaced apart positions on the bone mass, said second end portion having a head portion with a load transfer surface thereon and a top portion;
   b) an elongated plate member having upper and lower surfaces angled with respect to each other and an elongated plate slot having a longitudinally extending axis, a transverse cross section and a vertical centerline, said slot being surrounded by a peripheral portion having outer opposed edges;
   c) said slot defining an opening for receiving the bone screws, the plate member having a first and second angled sidewall at the slot, said sidewalls each forming an acute angle relative to the vertical centerline of the plate member whereby the slot is wider at the lower surface than at the upper surface.
   d) a washer interfacing with the plate member and each bone screw, for distributing load from each bone screw to the plate member, said washer including a central opening having a vertical centerline and upper and lower surfaces, said lower surface having a pair of laterally spaced apart projections extending therefrom;
   e) said plate member having a plurality of adjustment openings in the upper surface, and each of the washer projections sized and shaped to fit in selected pairs of adjustment openings;
   f) said angled plate sidewalls being angled to constrict bone screw angulation in a medial/lateral transverse plane when each bone screw interfaces with the washer and the washer interfaces with the plate member.

2. The apparatus of claim 1, wherein the slot is sized to accommodate a pair of spaced apart and surgically implantable bone screws that comprise the bone screws of the apparatus.

3. The apparatus of claim 1, wherein placement of the washer projections of each washer in selected pairs of the adjustment openings on the plate member provide for a fine adjustment means in the placement of each bone screw in relation to the bone mass.

4. The apparatus of claim 1, wherein the washer opening vertical centerline registers with the vertical centerline of the plate slot when the washer interfaces with the plate member.

5. The apparatus of claim 1, wherein the washer opening at the upper surface of the washer includes a hemispherical surface configured to register with the load transfer surface of the head portion of each bone screw, said hemispherical surface being configured to allow for angulation of each bone screw when the bone screw interfaces with the washer.

6. The apparatus of claim 5, wherein the hemispherical surface of the washer opening is configured so as to allow the rotation of the top portion of the screw head portion below the upper surface of the washer when the bone screw is angled.

7. The apparatus of claim 1, wherein the spaced apart projections of the washer are longitudinally offset from the washer opening centerline so as to allow for displacement of the washer opening centerline along the longitudinal axis of the plate member by rotating the washer 180° in a selected pair of adjustment openings of the plate member.

8. The apparatus of claim 1, wherein the first and second slot sidewalls are angled between about 15° to 45° relative to the vertical centerline of the plate member.

9. The apparatus of claim 8, wherein the first slot sidewall is angled 25° relative to the vertical centerline 0f the plate member and the second slot sidewall is angled 20° relative to the vertical centerline of the plate member.

10. The apparatus of claim 1, wherein the combination of a hemispherical surface of the washer opening and the transverse cross section and longitudinal axis of the plate slot, formed when the washer interfaces with the plate member, allows each bone screw inserted through the washer opening an elliptical rotational range between about 20° to 80° in the medial/lateral transverse plane and the cephalad/caudal longitudinal plane.

11. An angles bone screw fixation apparatus, comprising:
   a) a plurality of bone screws having a first end portion and a second end portion, said first end portion configured to be surgically implantable into a patient's vertebral bone mass and at first and second spaced apart positions on the bone mass, said second end portion having a head portion with a load transfer surface thereon and a top surface;
   b) an elongated plate member having upper and lower surfaces angled with respect to each other and an elongated plate slot having a longitudinally extending axis, a transverse cross section and a vertical centerline, said slot being surrounded by a peripheral portion having outer opposed edges;
   c) said slot defining on an opening for receiving the bone screws, the plate member having a first and second angular sidewall at the slot, each sidewall defining therebetween an angle of between about 15° to 45° relative to the vertical centerline of the plate member whereby the slot is wider at the lower surface than at the upper surface;

d) a washer interfacing with the plate member and each bone screw, for distributing load from each bone screw to the plate member, said washer including a central opening having a vertical centerline and upper and lower surfaces, said lower surface having a pair of laterally spaced apart projections extending therefrom;

e) said plate member having a plurality of adjustment openings in the upper surface, and each of the washer projections sized and shaped to fit in selected pairs of adjustment openings;

f) said angled plate sidewalls being angled to constrict bone screw angulation in a medial/lateral transverse plane when each bone screw interfaces with the washer and the washer interfaces with the plate member.

12. The apparatus of claim 11, wherein the slot is sized to accommodate a pair of spaced apart and surgically implantable bone screws that comprise the bone screws of the apparatus.

13. The apparatus of claim 11, wherein placement of the washer projections of each washer in selected pairs of the adjustment openings on the plate member provide for a fine adjustment means in the placement of each bone screw in relation to the bone mass.

14. The apparatus of claim 11, wherein the washer opening a vertical centerline registers with the vertical centerline of the plate slot when the washer interfaces with the plate member.

15. The apparatus of claim 11, wherein the washer opening on the upper surface of the washer includes a hemispherical surface configured to register with the load transfer surface of the head portion of each bone screw, said hemispherical surface being configured to allow for angulation of each bone screw when the bone screw interfaces with the washer.

16. The apparatus of claim 15, wherein the hemispherical surface of the washer opening is configured so as to allow the rotation of the top surface of the screw head portion below the upper surface of the washer when the bone screw is angled.

17. The apparatus of claim 11, wherein the spaced apart projections of the washer are longitudinally offset from the washer opening centerline so as to allow for displacement of the washer opening centerline along the longitudinal axis of the plate member by rotating the washer 180° in a selected pair of adjustment openings of the plate member.

18. The apparatus of claim 11, wherein the first slot sidewall is angled 25° relative to the vertical centerline of the plate member and the second slot sidewall is angled 20° relative to the vertical centerline of the plate member.

19. The apparatus of claim 11, wherein a combination of a hemispherical surface of the washer opening and the transverse cross section and longitudinal axis of the plate slot, formed when the washer interfaces with the plate member, allows each bone screw inserted through the washer opening an elliptical rotational range between about 20° to 80° in the medial/lateral transverse plane and the cephalad/caudal longitudinal plane.

20. An angled bone fixation apparatus, comprising:

a) a plurality of bone screws having a first end portion and a second end portion, said first end portion configured to be surgically implantable into a patient's vertebral bone mass and at first and second spaced apart positions on the bone mass, said second end portion having a head portion with a load transfer surface thereon and a top portion;

b) an elongated plate member having upper and lower surfaces angled with respect to each other and an elongated plate slot having a longitudinally extending axis, a transverse cross section and a vertical centerline, said slot being surrounded by a peripheral portion having outer opposed edges;

c) said slot defining, an opening for receiving the bone screws, the plate member having a first and second angled sidewall at the slot, said sidewalls each forming an acute angle relative to the vertical centerline of the plate member whereby the slot is wider at the lower surface than at the upper surface;

d) a washer interfacing with the plate member and each bone screw, for distributing load from each bone screw to the plate member, said washer including a central opening having a vertical centerline and upper and lower surfaces, said lower surface having a pair of laterally spaced apart projections extending therefrom;

e) said plate member having a plurality of adjustment openings in the upper surface, and each of the washer projections sized and shaped to fit in selected pairs of adjustment openings;

f) wherein a combination of the hemispherical surface of the washer opening and the transverse cross section and longitudinal axis of the plate slot, formed when the washer interfaces with the plate member, allows each bone screw inserted through the washer opening an elliptical rotational range between about 20° to 80° in the medial/lateral transverse plane and the cephalad/caudal longitudinal plane.

21. The angled bone fixation apparatus of claim 20, wherein said spaced apart projections of the washer are longitudinally offset from the washer opening centerline so as to allow for displacement of the washer opening centerlines along the longitudinal axis of the plate member by rotating the washer 180° in a selected pair of adjustment opening of the plate member.

* * * * *